(12) United States Patent
Shah et al.

(10) Patent No.: US 8,486,425 B1
(45) Date of Patent: Jul. 16, 2013

(54) TWO-PHASE SUNSCREEN COMPOSITION

(75) Inventors: Anil Shah, East Windsor, NJ (US); Ana Kljuic, New York, NY (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/569,326

(22) Filed: Aug. 8, 2012

(51) Int. Cl.
*A61K 8/02* (2006.01)
*A61K 31/74* (2006.01)

(52) U.S. Cl.
USPC .......................................................... 424/401

(58) Field of Classification Search
None
See application file for complete search history.

(56) References Cited

U.S. PATENT DOCUMENTS

| 2,463,264 A | 3/1949 | Graenacher et al. |
| 5,166,355 A | 11/1992 | Leistner et al. |
| 5,237,071 A | 8/1993 | Leistner et al. |

FOREIGN PATENT DOCUMENTS

| EP | 0832642 A2 | 4/1998 |
| EP | 0893119 A1 | 1/1999 |
| EP | 1008586 A1 | 6/2000 |
| EP | 1027883 A2 | 8/2000 |
| EP | 1133980 A2 | 9/2001 |
| EP | 1133981 A2 | 9/2001 |
| EP | 1300137 A2 | 4/2003 |
| GB | 2303549 A | 2/1997 |
| WO | 9304665 A1 | 3/1993 |
| WO | 03070201 A1 | 8/2003 |
| WO | 03070202 A1 | 8/2003 |
| WO | 2004054539 A1 | 7/2004 |
| WO | 2010069995 A1 | 6/2010 |

*Primary Examiner* — Susan Tran
(74) *Attorney, Agent, or Firm* — McNees Wallace & Nurick LLC

(57) ABSTRACT

The present invention is directed to two-phase sunscreen compositions containing (1) a water phase including an alcohol having five or fewer carbons and a polyol; and (2) an oil phase including at least one sunscreen active, a first emollient, and a second emollient, the first emollient having a first polarity, the second emollient having a second polarity, the first polarity differing from the second polarity. The present invention is also directed to a two-phase sunscreen product formed from the two-phase sunscreen composition and a method of protecting a keratinous substrate from UV radiation by applying onto a surface of the keratinous substrate the two-phase sunscreen product.

10 Claims, No Drawings

TWO-PHASE SUNSCREEN COMPOSITION

FIELD OF THE INVENTION

The present invention is directed to sunscreen compositions, sunscreen products, and the processes of protecting keratinous substrates. More specifically, the present invention is directed to two-phase sunscreens including at least one sunscreen active, a first emollient, and a second emollient possessing exceptional properties.

BACKGROUND OF THE INVENTION

Aging skin is the result of more than just chronological age. Skin is exposed to various environmental stresses, such as UV rays, which cause free radicals to form in the skin. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical which may attack adjacent fatty acids to generate new carbon radicals. This process can lead to a chain reaction producing lipid peroxidation products. Damage to the cell membrane can result in loss of cell permeability, increased intercellular ionic concentration and/or decreased ability to excrete or detoxify waste products. The end result is a loss of elasticity of the skin and the appearance of wrinkles leading to premature aging of the skin. This process is commonly referred to as photo-aging.

The degree of UV protection afforded by a composition is directly related to the amount and type of sunscreen actives present therein. The more sunscreen actives present, the greater the degree of UV protection. However, in order to incorporate significant amounts of sunscreen actives into a composition, a large amount of emulsifiers need to be used in order to make the composition stable so as to avoid separation and precipitation of ingredients. The use of significant amounts of emulsifiers, while making the composition more stable, detracts from the texture and feel of the composition when applied onto a keratinous substrate.

Compositions having two separate phases, a water phase and an oil phase, that emulsify readily by agitation are generally referred to by the term "two-phase composition." They differ from emulsions by the fact that at rest the two phases are separate instead of being emulsified in one another. Thus, the two phases are separated at rest by a single interface whereas, in emulsions, one of the phases is dispersed in the other in the form of a multitude of droplets, and the interfaces are therefore multiple, those interfaces generally being stabilized by emulsifying surfactants and/or emulsifying polymers. The use of two-phase compositions requires prior agitation in order to form an extemporaneous emulsion. This must be of sufficient quality and stability to allow a homogeneous application of the two phases, but such that at rest, the two phases rapidly separate and regain their initial state, this phenomenon being better known by the term "phase separation."

A number of known two-phase compositions form, after agitation, an opaque emulsion, which is a mixture of two phases that are immiscible in one another. However, these compositions are generally presented in transparent containers, and the opacity of the two emulsified phases is aesthetically unpleasant. Moreover, it is increasingly sought to use transparent compositions because, just like water, the transparency is a symbol of purity and therefore of cleanliness, and transparent compositions are thus particularly appreciated by the users.

The use, in two-phase compositions, of silicone oils, such as, for example, cyclopentasiloxane make it possible to obtain compositions that form, after agitation, a transparent mixture of two immiscible phases. However, it is difficult to obtain a transparent mixture when the two phases are not miscible, without using cyclic silicone oils.

Sunscreen actives are relatively polar and can cause preservatives to migrate from water phases to oil phases. This results in difficulty in preserving sunscreen formulations and can require high levels of preservatives. The high levels of preservatives can be harsh to human skin.

Conventional sunscreen compositions are expected to possess water-resistance properties in order to inhibit the protective composition from being easily removed from a keratinous substrate by sweat and exposure to water. In order to achieve this function, film-formers are typically employed in the composition. By forming a film on the surface of keratinous substrates, the sunscreen actives are more steadfastly held in place upon exposure to water. The use of film-formers; however, has a negative impact of the tactile properties of the composition, making the composition feel tacky to the user.

Multiple phase sunscreen compositions have been attempted in the art. For example, EP 831765, which is hereby incorporated by reference in its entirety, discloses a multi-phase sun screen composition, its production, and its application to the skin. EP 831765 includes at least two oily phases that are separate and are mixed prior to use on the skin. When mixed, the UV filters remain in the phase for which they were originally added. However, the sun screen composition of EP 831765 does not include water phases or an emollient combination resulting in a transparent composition having desirable sensory features.

WO/2003070201 and WO/2003070202, which are hereby incorporated by reference in their entirety, disclose a two-phasic sunscreen preparation comprising water/oil emulsions. The two-phase element includes a water/oil emulsion and a lipophilic phase. An emulsifier is included due to the inclusion of the water/oil emulsion. At least one of the two phases is not transparent, thus, it is not capable of being used in transparent applications.

WO/2010006995, which is hereby incorporated by reference in its entirety, discloses a silicon-free transparent two-phase composition. The composition includes an oil phase and a water phase, where both phases are initially transparent. Upon agitation, the two phases form a mixture that is transparent. To achieve such transparency the two-phase composition is formulated such that the reflective index of the oil phase and the water phase are substantially equal and result in a high amount of polyol (at least about 40%) being used. Such high loadings of polyol result in undesirable cosmetic features, such as an oily, a tacky or a heavy feel.

Thus, it is an object of the present invention to provide a composition and process for protecting cellular targets from aging and photo-damage caused by UV light, in general, and free radicals formed thereby, in particular.

It is yet another object of the present invention to provide a sunscreen composition which provides a significant degree of UV protection, while at the same time having a light, non-oily texture and skin feel property.

It is yet another object of the present invention to provide a sunscreen composition which possesses water-resistance properties but does not require the use of a film-former.

It is yet another object of the present invention to provide a sunscreen composition that is made up of two separate phases that are transparent and return to transparency after complete separation.

It is yet another object of the present invention to provide sunscreen composition which provides a significant degree of UV protection and is preservative free.

BRIEF DESCRIPTION OF THE INVENTION

The present invention is directed to a two-phase sunscreen composition containing:
1. a water phase including an alcohol having five or fewer carbons and a polyol; and
2. an oil phase including at least one sunscreen active, a first emollient, and a second emollient, the first emollient having a first polarity, the second emollient having a second polarity, the first polarity differing from the second polarity.

The present invention is also directed to a two-phase sunscreen product formed from the two-phase sunscreen composition and a method of protecting a keratinous substrate from UV radiation by applying onto a surface of the keratinous substrate the product two-phase sunscreen product.

Surprisingly, the Applicant has found that it was possible to obtain a two-phase composition which, is substantially transparent, cosmetically desirable and does not suffer from one or more of the above drawbacks by including at least one sunscreen active, a first emollient, and a second emollient, the first emollient having a first polarity, the second emollient having a second polarity, the first polarity differing from the second polarity.

Other features and advantages of the present invention will be apparent from the following more detailed description of the preferred embodiment, by way of example, the principles of the invention.

DETAILED DESCRIPTION OF THE INVENTION

The present invention is directed to a two-phase sunscreen composition, a sunscreen product, and a method of applying the sunscreen product as a physiologically acceptable medium that surprisingly and unexpectedly can be cosmetically desirable, can be transparent, can be photostable, can have low levels of or being devoid of surfactants/emulsifiers, can have low levels of or being devoid of preservatives, or any combination thereof.

Other than in the operating examples, or where otherwise indicated, all numbers expressing quantities of ingredients and/or reaction conditions are to be understood as being modified in all instances by the term "about".

"Keratinous substrate", as used here, includes, but is not limited to, skin, lips, hair, nails or any other cutaneous region of the body.

A "physiologically acceptable medium" means a medium which is not toxic and can be applied to the skin, lips, hair, scalp, lashes, brows, nails or any other cutaneous region of the body. The composition and/or product of the invention may especially constitute a cosmetic or dermatological composition.

One embodiment of the present invention includes a two-phase sunscreen composition having a water phase including an alcohol having five or fewer carbons and a polyol and an oil phase including at least one sunscreen active, a first emollient, and a second emollient, the first emollient having a first polarity, the second emollient having a second polarity, the first polarity differing from the second polarity. In addition, in another embodiment, the present invention includes a sunscreen product. The sunscreen product of the present invention is produced from the two-phase sunscreen composition of the present invention having a water phase and an oil phase. The sunscreen product is prepared according to any suitable technique.

Water Phase:

The water phase includes one or more of water, polyol, and alcohol. The water phase may further include additives, such as a chelating agents, and/or any other suitable water-soluble or water-dispersible additives.

A suitable concentration of the water phase in the composition is, by weight, between about 5% and about 70%, between about 10% and about 60%, between about 20% and about 50%, between about 30% and about 50%, between about 40% and about 50%, between about 40% and about 45%, between about 40% and about 43%, at about 41%, at about 42%, at 41.9%, or any suitable combination, sub-combination, range, or sub-range thereof.

The water phase of the composition includes suitable components to permit the water phase to be or become transparent after mixing and separation. Examples of percent transmissions for the water phase are at 700 nm being greater than about 99%, greater than about 99.5%, greater than about 99.9%, or any suitable combination, sub-combination, range, or sub-range thereof.

Water:

In addition to the polyols and the alcohol, the water phase also includes water. A suitable concentration of water is, by weight of the entire composition, between about 17% and about 23%, between about 17% and about 20%, between about 17% and about 19%, between about 17% and about 18%, between about 17.5% and about 18%, 17.8%, or any suitable combination, sub-combination, range, or sub-range thereof. The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Polyol:

The water phase further includes polyol. A suitable concentration of the polyol is, by weight of the entire composition, less than 40%, less than 20%, between about 10% and about 13%, between about 11% and about 13%, between about 11.5% and about 12.5%, or any suitable combination, sub-combination, range, or sub-range thereof. The term "polyol" should be understood to mean any organic molecule comprising at least two free hydroxyl groups. Suitable polyols include, for example, glycerol, glycols such as butylene glycol, propylene glycol, isoprene glycol, dipropylene glycol, hexylene glycol and polyethylene glycols, sorbitol, sugars such as glucose, and mixtures thereof. According to one preferred embodiment of the invention, the polyol chosen is glycerol, dipropylene glycol or mixtures thereof, or a mixture of glycerol and/or of dipropylene glycol and of one or more other polyols especially chosen from those indicated above: butylene glycol, propylene glycol, isoprene glycol, hexylene glycol, polyethylene glycols, sorbitol, sugars, methylpropanediol and 1,3-propanediol and mixtures thereof. A particularly suitable polyol for use with the present invention is glycerin.

Alcohol:

The water phase further includes alcohol having five or fewer carbons. A suitable alcohol is ethanol. A suitable concentration of the alcohol is, by weight of the entire composition, between about 3.0% and about 10.0%, about 5.0% and about 8.0%, between about 6.0% and about 8.0% or any suitable combination, sub-combination, range, or sub-range thereof.

Water Phase Additives:

The water phase may include any suitable water-soluble or water-dispersible additive, such as aloe and/or antioxidants. A suitable concentration of the aloe is, by weight of the entire composition, between about 4.0% and about 6.0%, between about 4.5% and about 5.5%, 4.75% about 5.0%, or any suitable combination, sub-combination, range, or sub-range thereof. Another suitable additive for addition to the water phase may include a chelating agent. The chelating agent may be any known chelating agent suitable for inclusion in the water phase of the composition. A suitable chelating agent for use in the composition according to the invention is ethylenediaminetetraacetic acid (EDTA). A suitable concentration of the chelating agent is, by weight of the entire composition, between about 0.05% and about 0.15%, or any suitable combination, sub-combination, range, or sub-range thereof.

Another additive that may be present in the water phase includes self-tanning agents that may be added to the composition for artificially tanning and/or browning the skin. An example of a self-tanning agent includes dihydroxyacetone (DHA). Artificial tanning agents are preferably present in amounts ranging from 0.1% to 10% by weight relative to the total weight of the composition.

Oil Phase:

The oil phase includes emollients, sunscreen actives, and oil soluble additives.

A suitable concentration of the oil phase in the composition is, by weight, between about 5% and about 70%, between about 10% and about 65%, between about 20% and about 60% or any suitable combination, sub-combination, range, or sub-range thereof.

The oil phase of the composition includes suitable components to permit the oil phase to be or become transparent after separation. The transparency of the oil phase includes percent transmissions of visible light at 700 nm greater than about 68%, greater than about 68.3%, or any suitable combination, sub-combination, range, or sub-range thereof.

Emollients:

The oil phase includes a ratio of emollients having dissimilar polarities to permit the composition to be or become transparent and have desirable sensory features. In one embodiment, the oil phase has a polarity profile based upon at least a first emollient having a first polarity and a second emollient having a second polarity, the first polarity differing from the second polarity. In one embodiment, the first emollient includes a polar emollient, such as a medium or high polarity emollient, and the second emollient includes a non-polar emollient, and preferably, dimethicone.

First Emollient: The first emollient may include a polar emollient. As used herein, "polar emollient" means any emollient having at least one polar moiety. The first emollient may be one or both of high and medium polarity oil soluble emollients. Suitable polar emollients include, but are not limited to, polyol esters and polyol ethers such as linear or branched chained polyglycerol esters and polyglycerol ethers. Particularly suitable emollients for use as the first emollient include caprylic/capric triglyceride, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopentanoate, $C_{12-15}$ alkyl benzoate, isopropyl lauroyl sarsosinate, phenethyl benzoate and mixtures thereof. Other suitable emollients include any oil soluble emollients having high or medium polarity moieties.

The oil phase may include a first emollient at a concentration of, by weight of the entire composition, between about 1.0% and about 10.0%, between about 2.0% and about 8.0%, between about 3.5% and about 4.5%, or any suitable combination, sub-combination, range, or sub-range thereof.

Second Emollient: The second emollient may include any suitable non-polar oil soluble emollients. "Non-polar emollient," as used herein, means any emollient possessing no permanent electric moments. Suitable non-polar emollients may include, but are not limited to, non-polar hydrocarbon, such as esters, linear or branched, or chained hydrocarbons. Non-limiting examples of such emollients may include paraffins, isoparaffins, mineral oil, silicone oils, dimethicone, isohexadecane, isododecane, diethylhexyl cyclohexane, and mixtures thereof. Particularly suitable emollients for use as the second emollient include one or more of dicaprylyl ether, isododecane, hydrocarbon, dimethicone and mixtures thereof. In other embodiments, the emollient includes non-silicone oils and dimethicone. In other embodiments, the second emollient includes dimethicone with one or more additional non-polar emollients.

The oil phase may include a second emollient at a concentration of, by weight of the entire composition, between about 15.0% and about 22.0%, between about 16.0% and about 20.0%, between about 17.0% and about 19.0%, or any suitable combination, sub-combination, range, or sub-range thereof. In addition, the oil phase may include dimethicone at a concentration of, by weight of the entire composition, between about 1.0% and about 5.0%, between about 1.0% and about 4.0%, between about 1.0% and about 3.0%, between about 1.5% and about 2.5%, about 2.0%, 2.0%, or any suitable combination, sub-combination, range, or sub-range thereof.

Polarity Ratio: A ratio of polar emollients to non-polar emollients to dimethicone (polar emollient:non-polar emollient:dimethicone), based on the total weight of the composition may be 2.0-5.0:16.0-19.0:1.0-3.0; 4.0:18.0:2.0; or 2.0:9.0:1.0.

Sunscreen Actives:

The sunscreen actives for use in the composition of the invention are typically organic. They may be present in an amount, as active material, a concentration of, by weight of the entire composition, between about 0.01% and about 40.0%, between about 0.1% and about 37.0%, between about 5.0% and about 35.0%, or any suitable combination, sub-combination, range, or sub-range thereof.

Sunscreen actives may include compounds such as, but not limited to, anthranilates; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. No. 5,237,071, U.S. Pat. No. 5,166,355, GB 2 303 549, DE 197 26 184 and EP 893 119; benzoxazole derivatives such as those described in patent applications EP 0 832 642; EP 1 027 883, EP 1 300 137 and DE 101 62 844; screening polymers and screening silicones such as those described especially in patent application WO 93/04665; dimers derived from α-alkylstyrene, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 1133 981, and mixtures thereof.

As examples of organic photoprotective agents, mention may be made of those denoted hereinbelow below their INCI name:

Dibenzoylmethane derivatives:
Butyl Methoxydibenzoylmethane (also known as avobenzone) sold especially under the trade name "PARSOL 1789" by Hoffmann LaRoche.

Benzotriazole derivatives, in particular, phenylbenzotriazole derivatives:
Drometrizole trisiloxane, marketed under the trademark "Silatrizole" by Rhodia Chimie or "Mexoryl XL" by L'Oreal.

Para-Aminobenzoic acid derivatives:
PABA, Ethyl PABA, Ethyl dihydroxypropyl PABA, Ethylhexyl dimethyl PABA sold in particular under the name "Escalol 507" by ISP, Glyceryl PABA, PEG-25 PABA sold under the name "Uvinul P25" by BASF.

Salicylic derivatives:
Homosalate sold under the name "Eusolex HMS" by Rona/EM Industries, Ethylhexyl salicylate sold under the name "Neo Heliopan OS" by Haarmann and Reimer, Dipropylene glycol salicylate sold under the name "Dipsal" by Scher, TEA salicylate sold under the name "Neo Heliopan TS" by Haarmann and Reimer.

β,β-Diphenylacrylate derivatives:
Octocrylene sold in particular under the trade name "Uvinul N539" by BASF, Etocrylene sold in particular under the trade name "Uvinul N35" by BASF.

Benzophenone derivatives:
Benzophenone-1 sold under the trade name "Uvinul 400" by BASF, Benzophenone-2 sold under the trade name "Uvinul D50" by BASF, Benzophenone-3 or Oxybenzone sold under the trade name "Uvinul M40" by BASF, Benzophenone-4 sold under the trade name "Uvinul MS40" by BASF, Benzophenone-5, Benzophenone-6 sold under the trade name "Helisorb 11" by Norquay, Benzophenone-8 sold under the trade name "Spectra-Sorb UV-24" by American Cyanamid, Benzophenone-9 sold under the trade name "Uvinul DS-49" by BASF, Benzophenone-12, Diethylaminohydroxybenzoylhexyl benzoate sold under the trade name "Uvinul A Plus" by BASF.

Benzylidenecamphor derivatives:
3-Benzylidenecamphor manufactured under the name "Mexoryl SD" by Chimex, 4-Methylbenzylidenecamphor sold under the name "Eusolex 6300" by Merck, Benzylidenecamphorsulfonic acid manufactured under the name "Mexoryl SL" by Chimex, Camphor benzalkonium methosulfate manufactured under the name "Mexoryl SO" by Chimex, Terephthalylidenedicamphorsulfonic acid manufactured under the name "Mexoryl SX" by Chimex, Polyacrylamidomethylbenzylidenecamphor manufactured under the name "Mexoryl SW" by Chimex.

Phenylbenzimidazole derivatives:
Phenylbenzimidazolesulfonic acid sold in particular under the trade name "Eusolex 232" by Merck, Disodium phenyl dibenzimidazole tetrasulfonate sold under the trade name "Neo Heliopan AP" by Haarmann and Reimer.

Phenylbenzotriazole derivatives:
Drometrizole trisiloxane sold under the name "Silatrizole" by Rhodia Chimie, Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals.

Triazine derivatives:
Bis(ethylhexyloxyphenol)methoxyphenyl triazine sold under the trade name "Tinosorb S" by Ciba-Geigy, Ethylhexyltriazone sold in particular under the trade name "Uvinul T150" by BASF, Diethylhexylbutamidotriazone sold under the trade name "Uvasorb HEB" by Sigma 3V, 2,4,6-tris(diisobutyl 4'-aminobenzalmalonate)-s-triazine.

Anthranilic derivatives:
Menthyl anthranilate sold under the trade name "Neo Heliopan MA" by Haarmann and Reimer.

Imidazoline derivatives:
Ethylhexyldimethoxybenzylidenedioxoimidazoline propionate.

Benzalmalonate derivatives:
Polyorganosiloxane containing benzalmalonate functions, for instance Polysilicone-15, sold under the trade name "Parsol SLX" by Hoffmann LaRoche.

4,4-Diarylbutadiene derivatives:
1,1-Dicarboxy(2,2'-dimethylpropyl)-4,4-diphenylbutadiene Benzoxazole derivatives:
2,4-bis[5-(1-dimethylpropyl)benzoxazol-2-yl(4-phenyl)imino]-6-(2-ethylhexyl)imino-1,3,5-triazine sold under the name Uvasorb K2A by Sigma 3V and mixtures thereof.

Oil Soluble Additives:
The oil phase may include any suitable oil-soluble additive. One example of suitable oil soluble additives includes tocopherol (vitamin E) at a concentration of, by weight of the entire composition, between about 0.05% and about 0.15%, about 0.1%, 0.1%, or any suitable combination, sub-combination, range, or sub-range thereof.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters (for instance the $C_{12}$-$C_{15}$ alkyl benzoate sold under the trade name "Finsolv TN" of "Witconol TN" by the company Witco, octyl palmitate, isopropyl lanolate and triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Additive components that may be additionally added to the oil phase further include:
antipollution agents and/or free-radical scavengers;
depigmenting agents and/or propigmenting agents;
antiglycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
tensioning agents;
moisturizers;
anti-inflammatory agents;
agents acting on the energy metabolism of cells; and/or
insect repellants.

A person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The sunscreen product formed by the water phase and the oil phase is capable of being applied to humans by spraying, thereby protecting a keratinous substrate from UV radiation by applying the sunscreen product onto a surface of the keratinous substrate.

The compositions described above may be packaged, in a known manner, in a single-compartment bottle. The user must then shake the bottle before pouring or spraying the product onto skin. The product may also be packed in a bottle of the "pump dispenser" type. Provision may also be made for the two phases of the composition to be introduced into two independent compartments of the same bottle, a system being provided to mix them together at the time of dispensing. Such devices are described, for example, in documents EP-A-497 256 and FR-A-2 697 233.

The composition, the sunscreen product, or both may be devoid of one or both of emulsifiers and preservatives. The composition, the sunscreen product, or both may be photostable.

The composition, the sunscreen product, or both may have a sun protection factor (spf) (in vivo) of greater than about 30, greater than about 40, between about 40 and about 45, greater than about 41, about 42, or any suitable combination, sub-combination, range, or sub-range thereof.

The composition, the sunscreen product, or both may have a persistent pigment darkening (PPD) value of greater than about 8.

The composition or product after mixing, may be transparent. For example, the water phase, the oil phase, or a combination thereof, immediately after separating or after a fixed duration after mixing (such as, about one hour, about four hours, about one day, about several days) is transparent. For example, the water phase, initially after separating, may have a percent transmission at 700 nm that is greater than about 81% or any suitable combination, sub-combination, range, or sub-range thereof. In addition, the oil phase, initially after separating, may have a percent transmission at 700 nm that is greater than about 63%, or any suitable combination, sub-combination, range, or sub-range thereof.

The following examples are intended to further illustrate the present invention. They are not intended to limit the invention in any way. Unless otherwise indicated, all parts are by weight.

EXAMPLES

The following examples are intended to further illustrate the present invention. They are not intended to limit the invention in any way. Unless otherwise indicated, all parts are by weight.

TABLE 1

INVENTIVE COMPOSITIONS

| Phase | Compound | Example 1 wt % | Example 2 wt % | Example 3 wt % |
|---|---|---|---|---|
| water | water | 17.8 | 19.8 | 19.8 |
| water | EDTA | 0.1 | 0.1 | 0.1 |
| water | polyol | 12.0 | 12.0 | 12.0 |
| water | alcohol | 7.0 | 5.0 | 5.0 |
| water | water soluble extract | 5.0 | 5.0 | 5.0 |
| oil | octocrylene | 5.0 | 5.0 | 5.0 |
| oil | avobenzone | 3.0 | 3.0 | 3.0 |
| oil | octisalate | 5.0 | 5.0 | 5.0 |
| oil | oxybenzone | 6.0 | 6.0 | 6.0 |
| oil | homosalate | 15.0 | 15.0 | 15.0 |
| oil | caprylic/capric triglyceride | 4.0 | 0.0 | 0.0 |
| oil | dicaprylyl ether | 0.0 | 3.0 | 0.0 |
| oil | isopropyl myristate | 0.0 | 0.0 | 4.0 |
| oil | PPG-3 myristyl ether | 0.0 | 0.0 | 0.0 |
| oil | non-polar hydrocarbon | 18.0 | 18.0 | 16.0 |
| oil | dimethicone | 2.0 | 3.0 | 4.0 |
| oil | antioxidant | 0.1 | 0.1 | 0.1 |
| | TOTAL | 100.0 | 100.0 | 100.0 |
| Transparency After Separation | | transparent | transparent after a few days | transparent after a few days |
| Weight Ratio of polar emollient/nonpolar emollient/dimethicone | | 4.0/18.0/2.0 | 3.0/18.0/3.0 | 4.0/16.0/4.0 |

The above compositions were combined, mixed and permitted to separate. After separation of the oil phase and the water phase, the compositions were observed for transparency.

TABLE 2

COMPARATIVE COMPOSITIONS

| Phase | Compound | Example 4 wt % | Example 5 wt % | Example 6 wt % | Example 7 wt % | Example 8 wt % | Example 9 wt % |
|---|---|---|---|---|---|---|---|
| water | water | 21.5 | 22.8 | 19.8 | 19.8 | 20.8 | 17.8 |
| water | EDTA | 0.1 | 0.1 | 0.1 | 0.1 | 0.1 | 0.1 |
| water | polyol | 10 | 10 | 12 | 12 | 12 | 12 |
| water | alcohol | 6.3 | 5 | 5 | 5 | 6 | 7 |
| water | water soluble extract | 4 | 5 | 5 | 5 | 4 | 5 |
| oil | octocrylene | 5 | 5 | 5 | 5 | 5 | 5 |
| oil | avobenzone | 3 | 3 | 3 | 3 | 3 | 3 |
| oil | octisalate | 5 | 5 | 5 | 5 | 5 | 5 |
| oil | oxybenzone | 6 | 6 | 6 | 6 | 6 | 6 |
| oil | homosalate | 15 | 15 | 15 | 15 | 15 | 15 |
| oil | caprylic/capric | 0 | 0 | 0 | 0 | 0 | 0 |

TABLE 2-continued

COMPARATIVE COMPOSITIONS

| Phase | Compound | Example 4 wt % | Example 5 wt % | Example 6 wt % | Example 7 wt % | Example 8 wt % | Example 9 wt % |
|---|---|---|---|---|---|---|---|
| oil | triglyceride | | | | | | |
| oil | dicaprylyl ether | 0 | 0 | 0 | 0 | 0 | 2 |
| oil | isopropyl myristate | 0 | 0 | 0 | 0 | 0 | 0 |
| oil | PPG-3 myristyl ether | 7 | 8 | 5 | 2 | 7 | 2 |
| oil | non-polar hydrocarbon | 13 | 10 | 15 | 20 | 13 | 18 |
| oil | dimethicone | 4 | 5 | 4 | 2 | 3 | 2 |
| oil | antioxidant | 0.1 | 0.1 | 0.1 | 0.1 | 0.1 | 0.1 |
| | TOTAL | 100 | 100 | 100 | 100 | 100 | 100 |
| Transparency After Separation | | not transparent | not transparent | not transparent | not transparent | not transparent | not transparent |
| Weight Ratio of polar emollient/nonpolar emollient/dimethicone | | 7.0/13.0/4.0 | 8.0/10.0/5.0 | 5.0/15.0/4.0 | 2.0/20.0/2.0 | 7.0/13.0/3.0 | 2.0/20.0/2.0 |

The above compositions were combined, mixed and permitted to separate. After separation of the oil phase and the water phase, the compositions were observed for transparency.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A two-phase sunscreen composition, comprising:
a water phase including an alcohol having five or fewer carbons and a polyol; and
an oil phase including at least one sunscreen active, a first emollient, and a second emollient, the first emollient having a first polarity, the second emollient having a second polarity, the first polarity differing from the second polarity;
wherein the first emollient is a polar emollient, the second emollient is a non-polar emollient and further includes dimethicone, the ratio of polar emollients to non-polar emollients to dimethicone, based on the total weight of the composition being 2.0-5.0:16.0-19.0:1.0-3.0;
wherein the two-phase sunscreen composition does not require emulsifiers or preservatives to form a photostable composition and wherein the two-phase sunscreen composition has a sun protection factor of greater than about 30.

2. The two-phase sunscreen composition of claim 1, wherein the two-phase sunscreen composition has a ratio of polar emollients to non-polar emollients to dimethicone of 4.0 to 18.0 to 2.0.

3. The two-phase sunscreen composition of claim 1, wherein the first emollient includes caprylic/capric triglyceride.

4. The two-phase sunscreen composition of claim 1, wherein the second emollient includes a non-silicone oil.

5. The two-phase sunscreen composition of claim 1, wherein the oil phase after separation includes percent transmissions of visible light at 700 nm greater than about 63%.

6. The two-phase sunscreen composition of claim 1, wherein the water phase after separation includes percent transmissions of visible light at 700 nm greater than about 81%.

7. The two-phase sunscreen composition of claim 1, wherein the two-phase sunscreen composition includes less than, by weight, about 40% being a polyol component.

8. The two-phase sunscreen composition of claim 1, wherein the two-phase sunscreen composition has a persistent pigment darkening of greater than about 8.

9. A two-phase sunscreen product formed from a two-phase sunscreen composition comprising:
a water phase including an alcohol having five or fewer carbons and a polyol; and
an oil phase including at least one sunscreen active, a first emollient, and a second emollient, the first emollient having a first polarity, the second emollient having a second polarity, the first polarity differing from the second polarity;
wherein the first emollient is a polar emollient, the second emollient is a non-polar emollient and further includes dimethicone, the ratio of polar emollients to non-polar emollients to dimethicone, based on the total weight of the composition being 2.0-5.0:16.0-19.0:1.0-3.0;
wherein the two-phase sunscreen composition does not require emulsifiers or preservatives to form a photostable composition and wherein the two-phase sunscreen composition has a sun protection factor of greater than about 30.

10. A method of protecting a keratinous substrate from UV radiation comprising applying onto a surface of the keratinous substrate a two-phase sunscreen product formed from a two-phase sunscreen composition comprising:
a water phase including an alcohol having five or fewer carbons and a polyol; and
an oil phase including at least one sunscreen active, a first emollient, and a second emollient, the first emollient having a first polarity, the second emollient having a second polarity, the first polarity differing from the second polarity;

wherein the first emollient is a polar emollient, the second emollient is a non-polar emollient and further includes dimethicone, the ratio of polar emollients to non-polar emollients to dimethicone, based on the total weight of the composition being 2.0-5.0:16.0-19.0:1.0-3.0;
wherein the two-phase sunscreen composition does not require emulsifiers or preservatives to form a photostable composition and wherein the two-phase sunscreen composition has a sun protection factor of greater than about 30.

* * * * *